United States Patent [19]

Atkins

[11] 4,130,715
[45] Dec. 19, 1978

[54] TRICYCLIC TRISAMINOMETHANES

[75] Inventor: Thomas J. Atkins, Wilmington, Del.

[73] Assignee: E. I. Du Pont de Nemours and Company, Wilmington, Del.

[21] Appl. No.: 872,663

[22] Filed: Jan. 26, 1978

Related U.S. Application Data

[62] Division of Ser. No. 647,643, Jan. 7, 1976, Pat. No. 4,085,106.

[51] Int. Cl.$^2$ .................. C07D 497/18; C07D 478/18
[52] U.S. Cl. .................................................. 548/324
[58] Field of Search ........................................ 548/324

[56] References Cited

U.S. PATENT DOCUMENTS

| 2,393,826 | 1/1946 | Senkus | 548/324 |
|---|---|---|---|
| 2,816,896 | 12/1957 | McKay et al. | 548/324 |
| 3,932,451 | 1/1976 | Bigelow et al. | 548/324 |

OTHER PUBLICATIONS

Durham et al., Chem. Abst. 1967, vol. 67, No. 100121s.

Primary Examiner—Natalie Trousof
Assistant Examiner—N. Harkaway

[57] ABSTRACT

Polycyclic trisaminomethanes of the formula

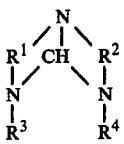

in which
$R^1$ and $R^2$, alike or different, are alkylene;
$R^3$ and $R^4$, alike or different, are alkyl, cycloalkyl, or aralkyl; or $R^3$ and $R^4$ are joined together to form an alkylene group which may be interrupted by
(1) a

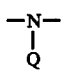

group where Q is hydrogen or alkyl, or
(2) one or two —O— linkages; and
there are at least 2 carbons between each two hetero atoms in the outer ring system, are useful as initiators for the polymerization of pivalolactone. These polycyclic trisaminomethanes are prepared by reacting a polyamine of the formula

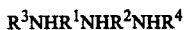

with a dialkoxy(dialkylamino)methane of the formula

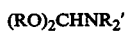

in which R and R', alike or different, are alkyl.

9 Claims, No Drawings

TRICYCLIC TRISAMINOMETHANES

CROSS-REFERENCE TO RELATED APPLICATION

This is a division of copending application Ser. No. 647,643, filed Jan. 7, 1976, now U.S. Pat. No. 4,085,106.

BACKGROUND OF THE INVENTION (1) Field of the Invention

This invention relates to polycyclic polyamines. More specifically, it relates to bicyclic and tricyclic trisaminomethanes, and to the method of their preparation.

(2) Description of the Prior Art

Polycyclic trisaminomethanes are known, but none in which the nitrogens are annular hetero atoms in a single large ring are known. The closest prior art references are:

1. Stetter and Bremen, Chem. Ber., 106, 2523 (1973), disclose the following reaction:

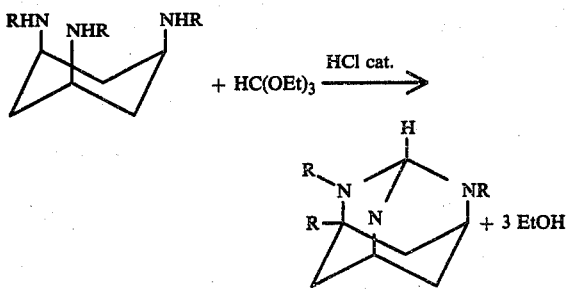

in which R = CH₃ or C₆H₅CH₂

2. Leimgruber and Wick, U.S. Pat. No. 3,726,924 (Hoffmann-La Roche, 1973), discloses the reaction of dimethylformamide dimethyl acetal with excess dimethylamine in the presence of an acidic catalyst to give tris(dimethylamino)methane.

$$(CH_3)_2NH + HC(OCH_3)_2N(CH_3)_2 \rightarrow$$
$$HC[N(CH_3)_2]_3$$

3. Bredereck et al., Chem. Ber., 101, 3058 (1968), disclose the preparation of tris(dialkylamino)methanes in which the alkyl groups are methyl, ethyl, and propyl by the reaction of the corresponding alkoxybis(dialkylamino)methanes (aminal esters) with the dialkylamines:

$$(R_2N)_2CHOR + R_2NH \rightarrow (R_2N)_3CH + ROH$$

4. Meerwein et al., Ann., 641, 1 (1961), disclose amine exchange between dimethylformamide diethyl acetal and piperidine or morpholine at 190° C.:

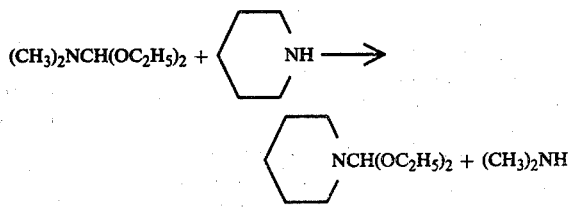

Only the dimethylamino group reacts; the ethoxy groups are not replaced.

SUMMARY OF THE INVENTION

In accordance with this invention, polycyclic trisaminomethanes have been discovered which are of the formula:

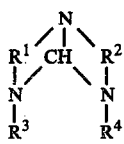

in which

R¹ and R², alike or different are alkylene of 2 to about 6 carbons containing at least 2 carbons in the backbone, and R³ and R⁴, alike or different, are alkyl of 1 to about 8 carbons, cycloalkyl of about 5 to about 8 carbons, or aralkyl where the aryl group is of 6 to about 12 carbons and the alkyl is of 1 to about 8 carbons, or R³ and R⁴ are joined together to form a divalent group selected from the group consisting of alkylene of 2 to about 6 carbons containing at least 2 carbons in the backbone,

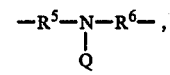

—R⁵-O-R⁶—, and

—R⁵-O-R⁶-O-R⁷ where

R⁵, R⁶ and R⁷, alike or different, are alkylene of 2 to about 6 carbons containing 2 to 3 carbons in the backbone, and Q is hydrogen or alkyl of 1 to about 18 carbons.

These polycyclic trisaminomethanes are prepared by contacting a polyamine of the formula

with a dialkoxy(dialkylamino)methane of the formula

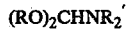

in which R and R', alike or different, are alkyl of 1 to about 4 carbons at a temperature of about 60° to about 150° C.

DETAILED DESCRIPTION OF THE INVENTION

For simplicity, and in accordance with the usual method of designating carbon atoms and any hydrogen atoms bonded to them, the formula for the products of this invention is usually written as

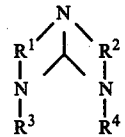

The three bonds from the nitrogens to the center of the ring system are understood to be connected to a CH grouping.

The compounds of this invention are bicyclic trisaminomethanes of the formula

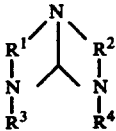

(1)

and, when $R^3$ and $R^4$ are joined together to form an alkylene group or interrupted alkylene group, the compounds are tricyclic trisaminomethanes of the formula

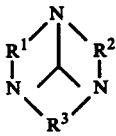

(2)

Examples of suitable $R^3$ and $R^4$ groups include alkyls such as methyl, propyl, t-butyl, and 1-ethyl-3-methylpentyl; cycloalkyls such as cyclopentyl and 2-methylcyclohexyl; and aralkyls such as benzyl, 1-naphthylmethyl, 1-methylphenethyl, and 7-phenylheptyl.

Suitable examples of $R^1$, $R^2$, and $R^8$ include alkylenes such as ethylene, trimethylene, tetramethylene, pentamethylene, hexamethylene, 1,2-dimethylethylene, 2,2-dimethyltrimethylene, and 1,3,3-trimethyltrimethylene. In compounds of formula (1) $R^1$ and $R^2$ are usually ethylene, $-CH_2CH_2-$, because of availability of the starting materials. When the compound is of formula (2), suitable examples of $R^8$ also include heteroalkylenes such as 3-azapentamethylene, 3-methyl-3-azapentamethylene, 3-octadecyl-3-azapentamethylene, 3-oxapentamethylene, 3,6-dioxaoctamethylene, and 3-oxahexamethylene. When $R^8$ is of the formula

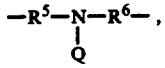

suitable examples of Q include hydrogen, methyl, ethyl, isopropyl, t-butyl, isopentyl, 2-ethylhexyl, dodecyl and octadecyl. Preferably Q is hydrogen or alkyl of 1 to about 8 carbons.

The products are prepared by the process of this invention which comprises reacting the appropriate polyamine with a dialkylformamide acetal, i.e., a dialkoxy(dialkylamino)methane. The reaction that takes place can be represented by the following equation:

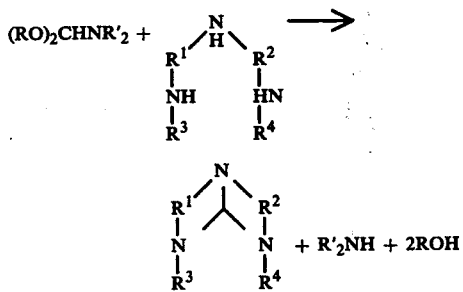

In the dialkylformamide acetal, the alkyl groups (R') bonded to nitrogen and the alkoxy groups (RO) will usually contain from 1 to about 4 carbons each. Ethyl and methyl are preferred species of R and R'. Methyl is an especially preferred species of R', since the dimethylamine by-product is very easily removed from the reaction mixture because of its low boiling point, about 7° C. Higher dialkylformamide acetals and acetals of glycols could be used, but no advantage would result, and removal of the higher-boiling amines and alcohols from the reaction mixture is more difficult.

Examples of operable acetals are dimethylformamide dimethyl acetal, dimethylformamide diethyl acetal, dimethylformamide dibutyl acetal, diethylformamide dimethyl acetal, diethylformamide dipropyl acetal, diethylformamide diisobutyl acetal, dipropylformamide dimethyl acetal, and dibutylformamide diisopropyl acetal. The dimethyl and diethyl acetals of dimethylformamide are commercially available. The other dialkylformamide acetals can be made by well known procedures.

Suitable $\alpha$, $\omega$-dihydrocarbyldialkylenetriamines of the formula $R^3$-NH-$R^1$-NH-$R^2$-NH-$R^4$ for forming the bicyclic triamines of formula (1) are known, for example, 1,7-dimethyldiethylenetriamine, 1,7-bis(1-methylheptyl)-diethylenetriamine, 1,7-dicyclopentyldiethylenetriamine, and 1,7-dibenzyldiethylenetriamine. These starting materials may be prepared by known alkylation methods such as reductive amination of an aldehyde or ketone. Reductive amination of an aldehyde is carried out in accordance with the equation:

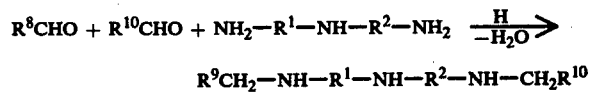

$R^9CH_2-NH-R^1-NH-R^2-NH-CH_2R^{10}$ where $R^9CH_2-$ and $R^{10}CH_2-$ are $R^3$ and $R^4$ respectively.

The diethylenetriamine starting material can be prepared by known methods. The higher dialkylenetriamines can be prepared by adaptations of these methods.

The cyclic polyamines used as starting materials for preparing the tricyclic trisaminomethanes of formula (2) are prepared by the method outlined by Richman and Atkins in J. Amer. Chem. Soc., 96, 2268 (1974). Suitable examples of these cyclic polyamines include 1-oxa-4,7,10-triazacyclododecane, 1,4-dioxa-7,10,13-triazacyclopentadecane, 1,4,7-triazacyclononane, 1,4,7-triazacyclodecane, 1,5,9-triazacyclododecane, 1,8,15-triazacycloheneicosane, 1,4,8-triazacycloundecane, 1,4,7,10-tetraazacyclododecane, and 1-oxa-4,7,10-triazacyclotridecane.

The reactants are usually and advantageously used in equimolar amounts. The process is operable when an excess of either reactant is used, but no advantage results, and isolation of the product is complicated by the presence of excess reactants. One mole of dialkylamine and two moles of the alcohol corresponding to the alkoxy groups in the acetal are formed as by-products.

As shown in the examples, the process can be carried out in the presence or absence of an inert solvent. Use of a solvent is sometimes advantageous in moderating the reaction and removing the by-product alcohol, and sometimes the by-product amine, via the formation of azeotropic mixtures. Operable solvents include aromatic hydrocarbons, such as benzene, toluene, and xylenes; aliphatic and cycloaliphatic hydrocarbons, such as hexane, heptane, isooctane, and cyclohexane; halohydrocarbons, especially chlorohydrocarbons, such as trichloroethylene, tetrachloroethylene, and chlorobenzene; dialkyl ethers, such as dipropyl ether and dibutyl ether, and alkanenitriles, such as acetonitrile and propionitrile. Aromatic hydrocarbons, particularly benzene, are a preferred group of solvents, since they are readily available and form homogeneous, well-defined azeotropes with the alcohols that are usually formed as by-products.

The process is operable over a range of temperatures from about 60° C. to about 150° C. or higher, the preferred range being about 80° to about 180° C. A convenient and useful temperature is the boiling temperature of the reaction mixture at atmospheric pressure.

A unique and unexpected feature of the process is that no catalyst is necessary. In related processes of the art, a catalyst, usually an acid catalyst, is required.

Since the reaction is an equilibrium process, removal of the by-products insures complete reaction. Essentially quantitative yields of the desired products are usually realized. The course of the reaction can be followed by measuring the amount of dialkylamine distilled off, e.g., by titration, and by noting the distillation temperature of the reaction mixture, which usually rises markedly after the alcohol has been completely removed. The time necessary for the reaction depends on both the rate of equilibration and the rate of by-product removal, which in turn depend on the temperature. Reactions times are usually of the order of about 2 to about 3 hours, but can be as short as about 15 to about 30 minutes.

The products of the invention are colorless, hygroscopic liquids and crystalline solids. They can conveniently be purified by distillation, and in some cases by recrystallization. These products are useful as nucleophilic initiators for anionic polymerizations such as the polymerization of pivalolactone.

EXAMPLES OF THE INVENTION

The following examples illustrate the products and process of the invention. All operations at or near atmospheric pressure were carried out under nitrogen, and all temperatures are in degrees Centigrade. In the equations accompanying the examples, the abbreviations Me and Et stand for $CH_3$ and $C_2H_5$, respectively.

EXAMPLE 1

10-Oxa-1,4,7-triazatricyclo[5.5.1.0$^{4,13}$]tridecane

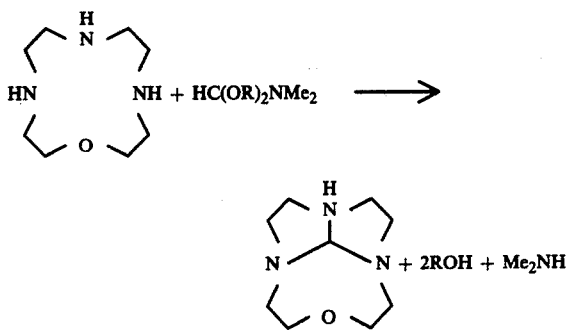

(A) A solution of 1.73 g (10 mmol) of 1-oxa-4,7,10-triazacyclododecane, 1.47 g (10 mmol) of dimethylformamide diethyl acetal (R = $C_2H_5$) and 35 ml of dry benzene was heated with stirring in a spinning-band distillation apparatus. The benzene-ethanol azeotrope, bp 67°-68°, was distilled off, and when the distillation temperature reached the boiling point of benzene (80°), the reaction mixture was removed and concentrated under reduced pressure to give 1.93 g of liquid. The product was distilled, bp 77°-79° (0.15 mm), $n_D^{25}$ = 1.5124; redistillation through a spinningband column gave analytically pure 10-oxa-1,4,7-triazatricyclo[5.5.1.0$^{4,13}$]tridecane, bp 90°-93° (0.30 mm).

Anal. Calcd for $C_8H_{17}N_3O$: C, 58.98; H, 9.35; N, 22.93. Found: C, 58.78; H, 9.67; N, 22.61.

An infrared spectrum (neat) showed major absorptions at 3.60, 6.83, 6.96, 7.30, 7.44, 7.60, 7.72, 8.01, 8.77, 9.10, 9.25, 9.37, 9.48, 9.82, 10.1, 10.3, 10.8, 11.2 and 11.9 μ.

An nmr spectrum at 220 MHz in $CDCl_3$/TMS (tetramethysilane) showed absorptions at δ4.31 (1H, s), 3.95 (2H, m), 3.56 (2H, m), 3.15 (2H, AA' pattern), 3.06 (2H, BB' pattern), 2.88 (2H, m), 2.84–2.71 (4H, m) and 2.64 (2H, m).

(B) In a manner similar to that of part (A), 5.00 g (28.9 mmol) of 1-oxa-4,7,10-triazacyclododecane and 3.45 g of dimethylformamide dimethyl acetal in 50 ml of dry benzene were reacted. The benzene-methanol azeotrope, bp 58°, was removed; the vapors showed the presence of a strongly basic gas with an ammonia odor ($Me_2NH$). After concentration, distillation of the residue gave 3.98 g (76% yield) of clear, colorless liquid, bp 160° (14 mm), which had the same ir spectrum as the material prepared in part (A).

(C) A mixture of 10.0 g of 1-oxa-4,7,10-triazacyclododecane and 6.90 g of dimethylformamide dimethyl acetal was heated under $N_2$ to 100° for 3 hr in a spinning-band distillation apparatus to remove methanol and dimethylamine. Distillation at reduced pressure afforded 8.59 g (81%) of clear, colorless liquid bp 86°-88° (0.25 mm), $n_D^{25}$ = 1.5159, whose ir was identical to that of the material prepared in part (A).

Anal. Found: C, 59.03; H, 9.37; N, 22,89.

If 1,4-dioxa-7,10,13-triazacyclopentadecane were used in place of 1-oxa-4,7,10-triazacyclododecane in essentially the procedure of Example 1, the product would be

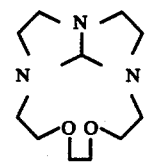

EXAMPLE 2

1,4,7-Triazatricyclo[5.2.1.0$^{4,10}$]decane

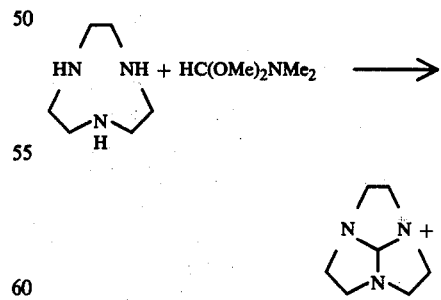

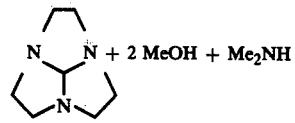

(A) A reaction mixture of 4.00 g (31 mmol) of 1,4,7-triazacyclononane (perhydro-1,4,7-triazonine), 3.70 g (31 mmol) of dimethylformamide dimethyl acetal and 50 ml of dry benzene was distilled through a spinning band column until the by-products and solvent were removed (dimethylamine, benzene-methanol azeotrope, bp 58°, and benzene, bp 80°). The residue was then distilled through a shortpath apparatus giving 3.68 g (86%) of clear, colorless liquid, bp 80°-82° (2.5 mm), $n_D^{24}$ = 1.5175. Redistillation of a small sample in a molecular still at 80° (0.4 mm) gave an analytical sample of 1,4,7-triazatricyclo[5.2.1.0$^{4,10}$]decane.

Anal. Calcd for $C_7H_{13}N_3$: C, 60.40; H, 9.41; N, 30.19 Found: C, 60.24; H, 9.46.

An infrared spectrum (neat) had major absorptions at 3.40, 6.67, 6.81, 7.47, 7.67, 7.85, 8.07, 8.33, 8.57, 9.06, 9.43, 9.56, 9.72, 10.71, 11.05 and 13.9 μ.

An nmr spectrum at 220 MHz in CDCl$_3$/TMS had absorptions at δ 5.03 (1H, s), 3.08 (6H, AA') and 2.80 (6H, BB').

(B) In a manner similar to that of Example 1 (C), 4.55 g (35.5 mmol) of 1,4,7-triazacyclononane and 4.20 g of dimethylformamide dimethyl acetal were reacted to give 4.33 g (88%) clear, colorless liquid, bp 79°-80° (2.6mm).

Anal. Found: N, 29.69.

EXAMPLE 3

1,4,7-Triazatricyclo[5.3.1.0$^{4,11}$]undecane

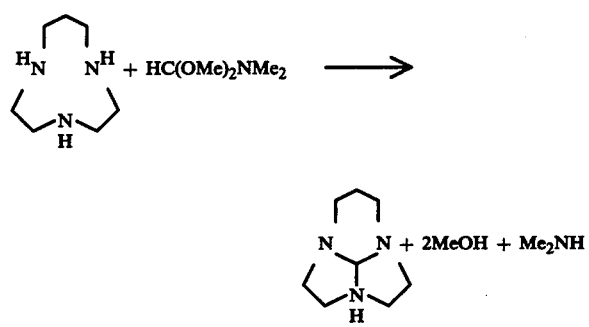

(A) In a manner similar to that of Example 2 (A), 4.80 g (33.5 mmol) of 1,4,7-triazacyclodecane and 4.00 g of dimethylformamide dimethyl acetal were reacted to give 4.67 g (91%) of clear, colorless liquid, bp 96°-97.5° (4.0 mm). Redistillation in a molecular still at 70° (3.4 mm) gave an analytical sample of 1,4,7-triazatricyclo[5.3.1.0$^{4,11}$]undecane.

Anal. Calcd for $C_8H_{15}N_3$: C, 62.71; H, 9.78; N, 27.42 Found: C, 61.27; H, 10.00; N, 27.10.

An infrared spectrum (neat) had major absorptions at 3.50, 6.83, 6.99, 7.32, 7.38, 7.90, 8.01, 8.28, 8.45, 8.56, 8.70, 9.09, 9.30, 9.65, 10.26, 10.8, 11.4 and 14.8 μ.

The nmr spectrum of this sample at 220 MHz in CDCl$_3$/TMS showed absorptions at δ4.04 (1H, s), 3.35 (2H, m), 3.17 (2H, m), 3.09-2.91 (4H, m), 2.79 (2H, m), 2.63 (2H, m), 1.97 (1H, m) and 1.09 (1H, d of pent).

(B) In a manner similar to that of Example 1 (C), 1,4,7-triazatricyclo[5.3.1.0$^{4,11}$]undecane was obtained from 1.4.7-triazacyclodecane and dimethylformamide dimethyl acetal as a clear, colorless liquid, bp 71°-74° (1.0 mm), $n_D^{25}$ = 1.5171, and was identified by infrared and nmr spectral comparison with the material obtained in part (A).

Anal. Found: C, 62.80; H, 10.01; N, 27.02.

EXAMPLE 4

1,4,8-Triazatricyclo[6.3.1.0$^{4,12}$]dodecane

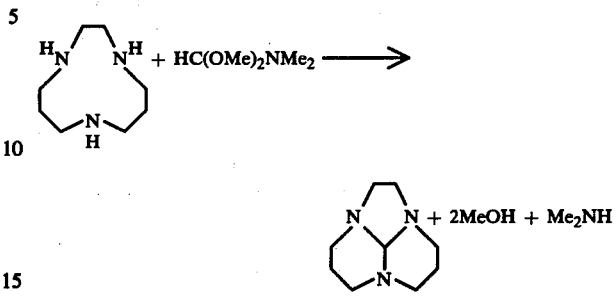

(A) In a manner similar to that of Example 1 (A), 3.30 g (21 mmol) of 1,4,8-triazacycloundecane, 2.50 g of dimethylformamide dimethyl acetal and 50 ml of dry benzene gave 3.14 g of clear, colorless liquid after two short-path distillations, bp 90°-98° (2.20 mm), $n_D^{24}$ = 1.5162, whose infrared spectrum was identical to that recorded in part (B) below.

(B) In a manner similar to that of Example 1 (C), 5.28 g (33.6 mmol) of 1,4,8-triazacycloundecane and 4.00 g of dimethylformamide dimethyl acetal were reacted to give 4.59 g of 1,4,8-triazatricyclo[6.3.1.0$^{4,12}$]dodecane as a clear, colorless liquid, bp 80°-82° (three fractions) (1.2 mm), $n_D^{24}$ = 1.5182. A fraction boiling at 82° was analyzed.

Anal. Calcd for $C_9H_{17}N_3$: C, 64.63; H, 10.25; N, 25.12. Found: C, 64.82; H, 10.52; N, 24.81.

An infrared spectrum (neat) had major absorptions at 3.40, 6.80, 7.30, 7.40, 7.65, 7.82, 7.93, 8.45, 8.75, 9.00, 9.11, 9.30, 10.76 and 10.97μ.

An nmr spectrum at 220 MHz in CDCl$_3$/TMS had absorptions at δ 3.20 (2H, q), 2.99 (2H, m), 2.80 (2H, m), 2.51 (2H, q), 2.49 (1H, s), 2.39 (2H, m), 1.98 (4H, m) and 1.43 (2H, m).

EXAMPLE 5

1,5,9-Triazatricyclo[7.3.1.0$^{5,13}$]tridecane

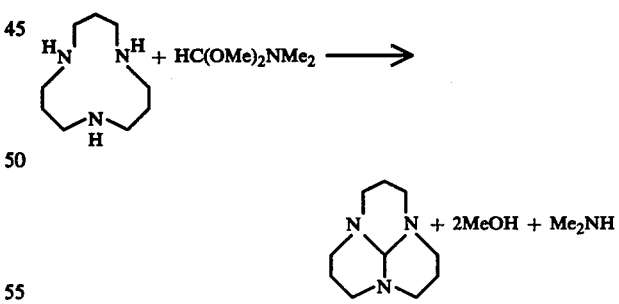

(A) In a manner similar to that of Example 1 (C), 5.00 g (29.2 mmol) of 1,5,9-triazacyclododecane and 3.48 g of dimethylformamide dimethyl acetal were reacted to give 3.87 g of 1,5,9-triazatricyclo[7.3.1.0$^{5,13}$]tridecane as a clear, colorless liquid, bp 93° (three fractions) (0.35 mm), which solidified on standing at room temperature. One fraction was analyzed.

Anal. Calcd for $C_{10}H_{19}N_3$: C, 66.26; H, 10.56; N, 23.18. Found: C, 66.56; H, 10.77; N, 23.49.

An infrared spectrum (neat) had major absorptions at 3.38, 3,55, 4.00 (w), 6.82, 6.98, 7.20, 7.37, 7.67, 7.78, 7.94, 8.21, 8.60, 8.88, 9.11, 10.2, 10.9, and 12.1μ.

At nmr spectrum at 220 MHz in CDCl₃/TMS had absorptions at 2.82 (6H, m), 2.31 (1H, s), 2.23–1.92 (9H, m) and 1.43 (3H, m).

(B) In a manner similar to that of Example 2 (A), 3.30 g (19.3 mmol) of 1,5,9-triazacyclododecane, 2.30 g of dimethylformamide dimethyl acetal and 50 ml of dry benzene gave 3.26 g of slightly yellow liquid, bp 115° (1.8 mm), $n_D^{24}$ = 1.5135, whose infrared spectrum was essentially the same as that recorded in part (A) above.

If 1,8,15-triazacycloheneicosane were used in place of 1,5,9-triazacyclododecane in essentially the procedure of Example 3, the product would be

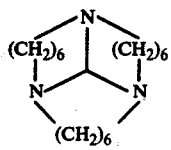

EXAMPLE 6

1,4,7,10-Tetraazatricyclo[5.5.1.0⁴,¹³]tridecane

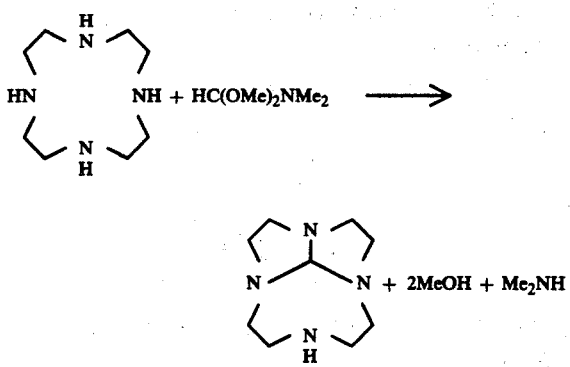

In a manner similar to that of Example 2 (A), 5.00 g (29.1 mmol) of 1,4,7,10-tetraazacyclododecane, 3.46 g of dimethylformamide dimethyl acetal and 50 ml of dry benzene gave 5.00 g of colorless liquid, bp 88.5°–90° (0.30 mm). Analytically pure 1,4,7,10-tetraazatricyclo[5.5.1.0⁴,¹³]tridecane was obtained by distillation of this material through a spinning band column, bp 82°–83° (two fractions) (0.25 mm) One fraction had $n_D^{25}$ = 1.5331. The other fraction was analyzed.

Anal. Calcd for C₈H₁₈N₄: C, 59.30; H, 9.95; N, 30.74. Found: C, 59.44; H, 10.19; N, 30.78.

An infrared spectrum (neat) had major absorptions at 2.97, 3.40, 3.52, 6.83, 6.95, 7.23, 7.44, 7.84, 7.95, 8.10, 8.44, 8.65, 9.11, 9.23, 10.3, 10.5, 10.8 and 11.1μ.

The nmr spectrum at 60 MHz in CDCl₃/TMS had absorptions at δ 4.45 (1H, s), 2.90 (16H, s) and 1.54 (1H, broad). In C₆D₆/TMS, the absorptions were at δ 4.80 (1H, s), 2.75 (16H, broad s, w ½ = 9 Hz) and 1.28 (1H, s).

If 1-ethyl-1,4,7,10-tetraazacyclododecane were used in place of 1,4,7,10-tetraazacyclododecane in essentially the procedure of part (A) above, the product would be of the formula

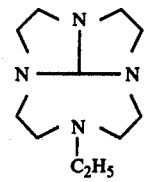

If 2,2,4,10,10,12-hexamethyl-1,5,9,13-tetraazacyclohexadecane were used in place of 1,4,7,10-tetraazacyclodecane in essentially the procedure of part (A) above, the product would be

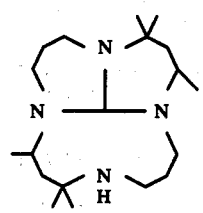

EXAMPLE 7

4,6-Dimethyl-1,4,6-triazabicyclo[3.3.0]octane

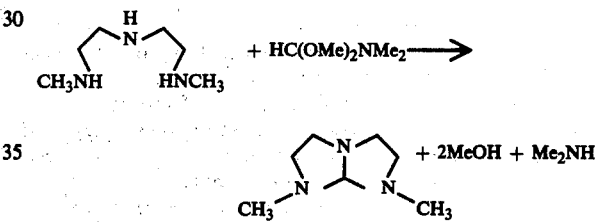

(A) In a manner similar to that of Example 2 (A), 9.29 g of 1,7-dimethyldiethylenetriamine, 8.44 g of dimethylformamide dimethyl acetal, and 50 ml of dry benzene gave 7.16 g (72%) of clear, colorless liquid, bp 71°–73° (13 mm).

An infrared spectrum in CCl₄ solution had major absorptions at 3.50, 6.87, 7.02, 7.31, 7.46, 8.01, 8.20, 8.35, 8.65, 8.81, 9.20, 9.40 and 11.14μ.

An analytical sample of 4,6-dimethyl-1,4,6-triazabicyclo[3.3.0]octane was obtained from a similar preparation.

Anal. Calcd for C₇H₁₅N₃: C, 59.54; H, 10.71; N, 29.76. Found: C, 58.92; H, 10.99; N, 29.69.

(B) In a manner similar to that of Example 1 (C), 11.01 g of 1,7-dimethyldiethylenetriamine and 10.0 g of dimethylformamide dimethyl acetal were reacted at 120° for 2 hr. Vacuum distillation of the residue gave 6.75 g of clear, colorless liquid, bp 47°–48° (2.8 mm), $n_D^{24}$ = 1.4742, which was identified by infrared spectral comparison with the product of part (A) above.

An nmr spectrum of this material at 220 MHz in CDCl₃/TMS showed absorptions at δ3.82 (1H, s), 3.50–2.55 (8H, m) and 2.38 (6H, s).

If 1,7-dicyclopentyldiethylenetriamine were substituted for 1,7-dimethyldiethylenetriamine in essentially the procedure of part (A) above, the product would be

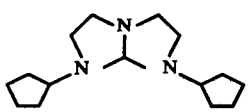

If 1,7-dibenzyldiethylenetriamine were substituted for 1,7-dimethyldiethylenetriamine in essentially the procedure of part (A) above, the product would be 4,6-dibenzyl-1,4,6-triazabicyclo[3.3.0]octane,

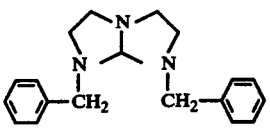

As shown in the following examples, the products of the invention are useful as initiators for the polymerization of pivalolactone.

EXAMPLE A

A solution of 10.0 g of pivalolactone and 0.017 ml (ca. 0.10 mole percent) of the product of Example 2 in 75 ml of hexane was allowed to stand for 4 days at 65° C. During this time polypivalolactone precipitated as a white solid.

EXAMPLE B

A reaction vessel fitted with a magnetic stirrer and a reflux condenser was charged with 10.0 g of pivalolactone and 75 ml of hexane at room temperataure. A solution of 0.14 g (1 mole percent) of the product of Example 7 in 2 ml of hexane was added by syringe, and the flask was immersed in a bath at 65° C., and stirred for 90 minutes. Polypivalolactone began to precipitate as a white solid after six minutes. The mixture was cooled to room temperature, and the polypivalolactone was isolated by filtration, washed with hexane, and air-dried. The yield was 4.36 g.

EXAMPLE C

The process of Example B was repeated with 0.17 g (1 mole percent) of the product of Example 4 as the initiator. The yield of polypivalolactone was 1.25 g.

What is claimed is:
1. A tricyclic trisaminomethane of the formula

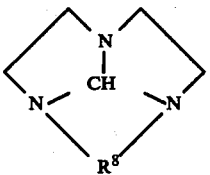

in which
R$^8$ is a divalent group selected from the group consisting of alkylene of 2 to 6 carbons containing 2 carbons in the backbone,

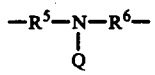

where
R$^5$ and R$^6$, alike or different, are alkylene of 2 to 6 carbons containing 2 carbons in the backbone, and Q is hydrogen or alkyl of 1 to 18 carbons, and

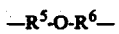

where
R$^5$ and R$^6$, alike or different, are alkylene of 2 to 6 carbons containing 2 to 3 carbons in the backbone.

2. The tricyclic trisaminomethane of claim 1 of the formula

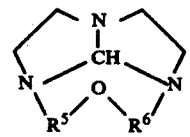

3. The tricyclic trisaminomethane of claim 2 in which R$^5$ and R$^6$, alike or different, are alkylene of 2 to 3 carbons.

4. The tricyclic trisaminomethane of claim 3 of the formula

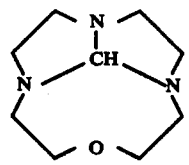

5. The tricyclic trisaminomethane of claim 1 of the formula

6. The tricyclic trisaminomethane of claim 5 in which R$^5$ and R$^6$, alike or different, are alkylene of 2 to 3 carbons, and Q is H or alkyl of 1 to 8 carbons.

7. The tricyclic trisaminomethane of claim 6 of the formula

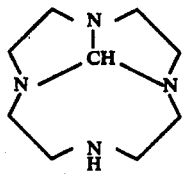

8. The tricyclic trisaminomethane of claim 6 of the formula

13
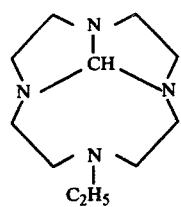
14
9. The tricyclic trisaminomethane of claim 1 of the formula
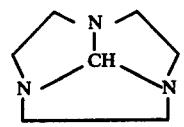
* * * * *